United States Patent [19]

Servier

[11] 4,430,431
[45] Feb. 7, 1984

[54] PRODUCING FUSAFUNGINE

[75] Inventor: Jacques P. Servier, Neuilly sur Seine, France

[73] Assignee: Biofarma, Neuilly sur Seine, France

[21] Appl. No.: 366,371

[22] Filed: Apr. 7, 1982

[30] Foreign Application Priority Data

Apr. 7, 1981 [FR] France .................................. 81 06917

[51] Int. Cl.$^3$ .......................... C12P 1/02; C12N 1/14; C12R 1/77
[52] U.S. Cl. .................................... 435/171; 435/254; 435/929
[58] Field of Search ........................ 435/171, 254, 929

[56] References Cited

U.S. PATENT DOCUMENTS 3,385,764  5/1968  Servier ................................ 435/171
3,737,523  6/1973  Cole et al. ........................ 435/929 X

FOREIGN PATENT DOCUMENTS 1164181  10/1958  France .
1392717   2/1965  France .

OTHER PUBLICATIONS

Chemical Abstracts, vol. 88, No. 19 (1978), 133170u.
The American Type Culture Collection–Catalogue of Strains I, 13th Ed. (1978), ATCC: Rockville, Md., p. 274.

*Primary Examiner*—Joseph M. Golian
*Attorney, Agent, or Firm*—Gordon W. Hueschen

[57] ABSTRACT

The invention relates to a new strain of Fusarium which is characterized by particular morphological, genetic and biochemical data. It is used for the production of antibiotics, especially of fusafungine.

1 Claim, No Drawings

PRODUCING FUSAFUNGINE

The present invention is concerned with a new micro-organism which is cultivated for the production of antibiotics, and more specially of fusafungine, an antibiotic for external use for the treatment of disorders of the throat.

Fusafungine and its preparation from *Fusarium lateritium* have been described in particular in French Pat. No. 1,164,181 and this micro-organism has been filed at the Centraalbureau Voor Schimmelcultures at Baarn under the No. CBS 119,63. Furthermore, French Pat. No. 1,392,717 describes the improvements made to the industrial preparation process of fusafungine from the latter strain, that is, improved yields of 0.5 to 0.8 g/l.

Various processes have been tested which have not enabled the yield to be increased, because fusafungine, a constituent of the body of the Fusarium, is present in each strain in a characteristic concentration which cannot be increased by the preparation process beyond the point at which it recovers all the fusafungine present in the preparation.

Other strains have been tested which have not had a more advantageous yield, and have had more difficult cultural conditions.

The invention aims at making available a strain which produces a larger quantity of fusafungine of equal quality—and by the same preparation process.

The applicant has succeeded in obtaining a new strain meeting this criterion. The aim is achieved to the extent that the older strains gave yields of the order of 0.1 to 0.2 g/l of fusafungine in the laboratory, and the new strain gives 0.6 to 0.9 g/l, that is to say, a yield averaging 6 times greater. On an industrial scale 1.8 to 3.6 kg/m$^3$ could be obtained, that is to say at least 3 to 4 times more than according to French Pat. No. 1,392,717. The new strain according to this invention has been obtained from strain CBS 119,63 by separation, isolation of colonies and seeding on different supports.

Starting with spores sampled from different supports capable of containing mutagenic agents, seedings have been made on agar mediums to obtain isolated colonies. These have been tested on production mediums. The yield and the composition of the fusafungine produced have been determined.

The strain, which is the subject of the invention, has been retained. It has now been stabilized by lyophilization on separated milk.

According to its characteristics, this new strain belongs to the fusarium type. It has been filed and identified at the Centraalbureau Voor Schimmelcultures at Baarn under No. CBS 675.80

The present strain cannot be identified with any of the known species, and it is a new species which the applicant has called *Fusarium lateritium servier.*

MORPHOLOGICAL STUDY

The new strain, *Fusarium lateritium servier* CBS 675.80 is of a dark colour, the sporulation has a sporodochium aspect with tufts of aerial mycelium, while the original strain filed at the Centraalbureau Voor Schimmelcultures at Baarn under No. 119.63 is light-coloured, its culture is smooth, and the sporulation is of pionnote type.

GENETIC STUDY

The important biochemical characteristics of production of fusafungine is transmitted genetically. It therefore is characteristic of a difficult genome.

The transmission of these characteristics through three successive generations while comparing them with two other known strains cultivated simultaneously and planted out again on 3 generations in identical conditions, has been verified by the following procedure:

The wild species, CBS 119.63, preserved on quince-tree- or acacia-compost was isolated from its preservation medium by passage on a Scheffer liquid medium, before being seeded on a agar enriched with oatmeal, to serve as a reference.

The *Fusarium lateritium servier* having been seeded directly on oatmeal agar, the following procedures were identical for the three species: isolation of an element, seeding at the end of the cycle, extraction of the greater part for fermentation and analysis, isolation of an element and re-seeding on a new agar.

The procedure is the same at the end of the second generation for obtaining a third generation.

The fermentation procedures were identical for the three generations of the three strains and used the same medium.

The following table summarizes the results:

| Strain | Production of Fusafungine per liter of medium (in g) | | |
|---|---|---|---|
| | 1st generation | 2nd generation | 3rd generation |
| *F. Lateritium* CBS 119.63 (On quince-tree compost) | 0.1 | 0.12 | 0.09 |
| Same (acacia-compost) | 0.14 | 0.17 | 0.13 |
| *F. Lateritium* Servier (CBS 675.80) | 0.710 | 0.605 | 0.826 |

BIOCHEMICAL STUDY

The very large quantity of fusafungine present, greater than all known concentrations in other strains, constitutes a biochemical characteristic of its originality.

It has been established that the fusafungine produced by this strain is identical to that produced by the other different species used for the production of fusafungine as much by its color, its melting point, its antibiotic power and its absorption spectra of electromagnetic, infra-red and ultraviolet waves.

PREPARATION OF THE FUSAFUNGINE

The strain of *Fusarium lateritium servier* can be conserved in lyophilized form in sealed ampoules.

The contents of the lyophilized ampoule can be used to seed directly an enriched agar tube as obtainable commercially or by standard techniques.

The mycelium develops progressively, and after a cycle of 15 to 20 days it can serve to re-seed another tube in order to obtain fermentation. A medium made up in the following way is used.

Saccharose 25 g/l
Spongy glucose 25 g/l
Ammonium nitrate 10 g/l
Monopotassium Phosphate 5 g/l
Magnesium Sulphate 2.5 g/l
The spontaneous pH is then 5.4 to 5.5.

The medium is then sterilized for 30 minutes at 120° C., and its pH becomes 4.8 to 5.

The medium is seeded and its temperature is fixed at 28° C.

Aeration is provided at the rate of 1 liter of air/minute/liter of medium and fermentation is allowed for 95±5 hours—until the carbohydrates are exhausted.

After fermentation, the mycelium is extracted with a chlorinated solvent. The extraction solvent is eliminated by evaporation under reduced pressure and the residue is dissolved in a hydrocarbon from which it is re-extracted with an aqueous alcohol.

Concentrating the aqueous alcohol causes precipitation of the crude product.

Purification is achieved by treatment with alcoholic solution with activated carbon specially treated for this purpose. The purified product is re-crystallized from an ethyl alcohol-water mixture.

Characterization:

M.P. = 128°–131° C.

Rotatory power: $[\alpha]_D^{20} = -94°$ to $-104°$ (2% in $CHCl_3$).

I.R. spectra ($\mu$): 3.4, 5.8, 6.0, 6.8, 7.3, 7.7, 8.0, 8.5, 9.0, 9.2, 10.0, 11.6.

The invention also includes a biologically pure cultures of *Fusarium lateritium servier*, the characteristics of which correspond to those of the strain identified under No. CBS 675.80 and which can also produce the antibiotic substance by fermentation in a nutritive medium.

The strain which is the subject of the invention can be used for the preparation of compounds of biological origin, and more specially of fusafungine, which can be used in the pharmaceutical, cosmetic or alimentary industries, and to constitute a medicament, a food-stuff, or an additive.

The strain employed according to the invention can be mutated by known artificial mutation agents: ultraviolet and X-rays and various chemical substances such as nitrosoguanidines, mitomycine, etc., and all the mutants obtained which are capable of producing the antibiotic fusafungine can be used in carrying out the present invention.

What I claim is:

1. In a process for the production of the antibiotic fusafungine which includes the step of aerobically growing a fusafungine-producing strain of *Fusarium lateritium* in a synthetic nutrient medium, the improvement which comprises: employing, as the fusafungine-producing strain of *Fusarium lateritium*, the strain identified as *Fusarium lateritium servier* CBS 675.80.

* * * * *